US007968318B2

(12) United States Patent
Lantero et al.

(10) Patent No.: US 7,968,318 B2
(45) Date of Patent: Jun. 28, 2011

(54) PROCESS FOR CONVERSION OF GRANULAR STARCH TO ETHANOL (75) Inventors: Oreste J. Lantero, Beloit, WI (US); Mian Li, Beloit, WI (US); Jayarama K. Shetty, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 1185 days.

(21) Appl. No.: 11/447,554

(22) Filed: Jun. 6, 2006

(65) Prior Publication Data

US 2007/0281344 A1    Dec. 6, 2007

(51) Int. Cl.
C12P 19/14 (2006.01)
C12P 7/06 (2006.01)
C12Q 1/02 (2006.01)
C12Q 1/48 (2006.01)
C12Q 1/34 (2006.01)
C12Q 1/37 (2006.01)

(52) U.S. Cl. .............. 435/99; 435/161; 435/29; 435/23; 435/18; 435/15

(58) Field of Classification Search ................ 435/15, 435/18, 23, 29, 99, 161
See application file for complete search history.

(56) References Cited

U.S. PATENT DOCUMENTS

| | | | |
|---|---|---|---|
| 4,092,434 A | 5/1978 | Yoshizumi et al. | |
| 4,316,956 A | 2/1982 | Lutzen | |
| 4,514,496 A | 4/1985 | Yoshizumi et al. | |
| RE32,153 E | 5/1986 | Tamura et al. | |
| 4,587,215 A | 5/1986 | Hirsh | |
| 4,618,579 A | 10/1986 | Dwiggins et al. | |
| 4,863,864 A | 9/1989 | Ashikari et al. | |
| 5,000,000 A | 3/1991 | Ingram et al. | |
| 5,028,539 A | 7/1991 | Ingram et al. | |
| 5,093,257 A | 3/1992 | Gray | |
| 5,424,202 A | 6/1995 | Ingram et al. | |
| 5,514,583 A | 5/1996 | Picataggio et al. | |
| 5,554,520 A | 9/1996 | Fowler et al. | |
| 5,763,385 A | 6/1998 | Bott et al. | |
| 5,824,532 A | 10/1998 | Barnett et al. | |
| 5,863,533 A | 1/1999 | Van Gorcom et al. | |
| 5,958,739 A | 9/1999 | Mitchinson et al. | |
| 6,008,026 A | 12/1999 | Day | |
| 6,093,562 A | 7/2000 | Bisgård-Frantzen et al. | |
| 6,187,576 B1 | 2/2001 | Svendsen et al. | |
| 6,350,602 B1 | 2/2002 | Van Gorcom et al. | |
| 6,352,851 B1 | 3/2002 | Nielsen et al. | |
| 6,361,809 B1 | 3/2002 | Christophersen et al. | |
| 6,734,004 B2 | 5/2004 | Kostrewa et al. | |
| 6,867,031 B2 | 3/2005 | Bisgård-Frantzen et al. | |
| 7,413,887 B2 | 8/2008 | Dunn-Coleman et al. | |
| 2008/0318284 A1* | 12/2008 | Soong et al. | 435/96 |
| 2009/0098624 A1* | 4/2009 | Deinhammer et al. | 435/161 |

FOREIGN PATENT DOCUMENTS

| | | |
|---|---|---|
| EP | 0 171 218 A2 | 2/1986 |
| WO | WO 84/02921 A2 | 8/1984 |
| WO | WO 92/00381 A1 | 1/1992 |
| WO | WO 95/13362 A1 | 5/1995 |
| WO | WO 96/23874 A1 | 8/1996 |
| WO | WO 96/39528 A2 | 12/1996 |
| WO | WO 97/38096 A1 | 10/1997 |
| WO | WO 97/41213 A1 | 11/1997 |
| WO | WO 98/28408 A1 | 7/1998 |
| WO | WO 98/28409 A1 | 7/1998 |
| WO | WO 98/44125 A1 | 10/1998 |
| WO | WO 99/19467 A1 | 4/1999 |
| WO | WO 99/28488 A2 | 6/1999 |
| WO | WO 00/04136 A1 | 1/2000 |
| WO | WO 03/018766 A3 | 3/2003 |
| WO | WO 03/066826 A2 | 8/2003 |
| WO | WO 03/068976 A2 | 8/2003 |
| WO | WO 2004/080923 A2 | 9/2004 |
| WO | WO 2004/081193 A2 | 9/2004 |
| WO | WO 2004/106533 A1 | 12/2004 |
| WO | WO 2004/111218 A2 | 12/2004 |
| WO | WO 2005/001064 A2 | 1/2005 |
| WO | WO 2005/003311 A2 | 1/2005 |
| WO | WO 2005/045018 A1 | 5/2005 |
| WO | WO 2005/052148 A2 | 6/2005 |
| WO | WO 2005/069840 A2 | 8/2005 |
| WO | WO 2005/096804 A2 | 10/2005 |
| WO | WO 2005/117756 A2 | 12/2005 |
| WO | WO 2005/118800 A1 | 12/2005 |
| WO | WO 2006/043178 A2 | 4/2006 |

OTHER PUBLICATIONS

Perpète et al., "Influence of Beer Ethanol Content on the Wort Flavour Perception", Food Chemistry, 71 (2000) 379-385.*
Wikipedia, http://en.wikipedia.org/wiki/Starch_gelatinization pp. 1-3, printed Nov. 6, 2010.*
U.S. Appl. No. 11/102,188, filed Jan. 19, 2006, Ferrari, et al.
Allison, D.S. et al. "Transformation of the thermophilic fungus *Humicola grisea* var. *thermoidea* and overproduction of *Humicola* glucoamylase," *Current Genetics* 21(3):225-229, Mar. 1, 1992.
Ashikari, T. et al. "Rhizopus raw-starch-degrading glucoamylase:its cloning and expression in yeast," *Agricultural and biological chemistry* 50(4):957-964, 1986.
Berka, R.M. et al. "Molecular Characterization and Expression of a Phytase Gene from the Thermophilic Fungus *Thermomyces lanuginosus*,"*Appl. Environ. Microbiol.* 64(11):4423-4427, Nov. 1, 1998.
Boel, E. et al. "Glucoamylases G1 and G2 from *Aspergillus niger* are synthesized from two different but closely related mRNAs," *The EMBO Journal* 3(5):1097-1102, May 1984.

(Continued)

*Primary Examiner* — Jon P Weber
*Assistant Examiner* — Kailash C Srivastava
(74) *Attorney, Agent, or Firm* — Drinker Biddle & Reath LLP (57) ABSTRACT

A method is disclosed for producing glucose from a granular starch substrate including, contacting a slurry comprising granular starch obtained from plant material with an alpha-amylase at a temperature below the starch gelatinization temperature of the granular starch to produce oligosaccharides and hydrolyzing the oligosaccharides to produce a mash comprising at least 20% glucose and further comprising fermenting the mash to obtain ethanol.

28 Claims, 1 Drawing Sheet

OTHER PUBLICATIONS

Bothast, R.J. et al. "Biotechnological processes for conversion of corn into ethanol," *Applied Microbiology and Biotechnology* 67(1):19-25, Apr. 17, 2005.

Chen, H.M. et al. "Substitution of asparagine residues in *Aspergillus awamori* glucoamylase by site-directed mutagenesis to eliminate N-glycosylation and inactivation by deamidation," *Biochem. J.* 301(Pt 1):275-281, Jul. 1, 1994.

Chen, H.-M. et al. "Identification and elimination by site-directed mutagenesis of thermolabile aspartyl bonds in *Aspergillus awamori* glucoamylase," *Protein Eng.* 8(6):575-582, Jun. 1, 1995.

Chen, H.-M. et al. "Effect of replacing helical glycine residues with alanines on reversible and irreversible stability and production of *Aspergillus awamori* glucoamylase," *Protein Eng.* 9(6):499-505, Jun. 1, 1996.

Cornett, C.A.G. et al. "Starch-binding domain shuffling in *Aspergillus niger* glucoamylase," *Protein Eng.* 16(7):521-529, Jul. 1, 2003.

Greiner, R. et al. "Purification and characterization of two phytases from *Escherichia coli*," *Arch. Biochem. Biophys* 303(1):107-13, May 15, 1993.

Hata, Y. et al. "The glucoamylase cDNA from *Aspergillus oryzae*:its cloning, nucleotide sequence, and expression in *Saccharomyces cerevisiae*," *Agric. Biol. Chem.* 55(4):941-949, Apr. 1991.

Hayashida, S. et al. "Molecular cloning of the glucoamylase I gene of *Aspergillus awamori* var. *kawachi* for localization of the raw-starch-affinity site," *Agricultural and Biological Chemistry* 53(4):923-929, 1989.

Jensen, B. et al. "Purification of extracellular amylolytic enzymes from the thermophilic fungus *Thermomyces lanuginosus*," *Can. J. Microbiol.* 34(3):218-223, 1988.

Miller, G.L. "Use of Dinitrosalicylic Acid Reagent for Determination of Reducing Sugar," *Anal. Chem.* 31(3):426-428, Mar. 1, 1959.

Shibuya, I. et al. "Molecular cloning of the glucoamylase gene of *Aspergillus shirousami* and its expression in *Aspergillus oryzae*," *Agricultural and Biological Chemistry* 54(8):1905-1914, Aug. 1990.

Shibuya, I. et al. "Overproduction of an α-Amylase/Glucoamylase Fusion Protein in *Aspergillus oryzae* Using a High Expression Vector," *Bioscience, biotechnology, and biochemistry* 56(10):1674-1675, 1992.

Suzuki, Y et al. "Amino acid residues stabilizing a *Bacillus* alpha-amylase against irreversible thermoinactivation," *J. Biol. Chem.* 264(32):18933-18938, Nov. 15, 1989.

Swinkels, J.J.M. "Sources of Starch:Its Chemistry and Physics," In *Starch Conversion Technology*, edited by G.M.A. van Beynum et al., pp. 32-38. New York:M. Dekker, 1985.

Takahashi, T. et al. "Different Behavior towards Raw Starch of Three Forms of Glucoamylase from a *Rhizopus* Sp," *J Biochem* 98(3):663-671, Sep. 1, 1985.

Taylor, P.M. et al. "Some Properties of a Glucoamylase Produced by the Thermophilic Fungus *Humicola lanuginosa*," *Carbohydrate Research* 61:301-308, 1978.

Tosi, L.R.O. et al. "Purification and characterization of an extracellular glucoamylase from the thermophilic fungus *Humicola grisea* var. *thermoidea*," *Canadian Journal of Microbiology* 39(9):846-852, 1993.

Wodzinski, R.J. et al. "Phytase," In *Advances in Applied Microbiology*, edited by S.L. Neidleman et al., vol. 42:pp. 263-302. New York:Academic Press, 1996.

Wyss, M. et al. "Biochemical Characterization of Fungal Phytases (myo-lnositol Hexakisphosphate Phosphohydrolases):Catalytic Properties," *Appl. Environ. Microbiol.* 65(2):367-373, Feb. 1, 1999.

Yamada, K. et al. "Phytase from *Aspergillus terreus*," *Agr. Biol. Chem* 32(10):1275-1282, 1968.

Yoon, Seong Jun et al. "Isolation and identification of phytase-producing bacterium, Enterobacter sp. 4, and enzymatic properties of phytase enzyme," *Enzyme and Microbial Technology* 18(6):449-454, May 1, 1996.

* cited by examiner

PROCESS FOR CONVERSION OF GRANULAR STARCH TO ETHANOL

FIELD OF THE INVENTION

The present invention relates to processes for the production of an alcohol (e.g., ethanol) from a granular starch comprising exposing a slurry comprising granular starch from plant material to an alpha-amylase at a temperature below the gelatinization temperature of the granular starch followed by fermentation with a fermenting microorganism.

BACKGROUND OF THE INVENTION

The commercial viability of producing ethanol as a fuel source from agricultural crops has generated renewed worldwide interest due to a variety of reasons that include continued and increased dependence on limited oil supplies and the fact that ethanol production is a renewable energy source.

Alcohol fermentation production processes and particularly ethanol production processes are generally characterized as wet milling or dry milling processes. Reference is made to Bothast et al., 2005,Appl. Microbiol. Biotechnol. 67:19-25 and THE ALCOHOL TEXTBOOK, $3^{rd}$ Ed (K. A. Jacques et al. Eds) 1999 Nottingham University Press, UK for a review of these processes.

In general, the wet milling process involves a series of soaking (steeping) steps to soften the cereal grain wherein soluble starch is removed followed by recovery of the germ, fiber (bran) and gluten (protein). The remaining starch is further processed by drying, chemical and/or enzyme treatments. The starch may then be used for alcohol production, high fructose corn syrup or commercial pure grade starch.

In general, dry grain milling involves a number of basic steps, which include: grinding, cooking, liquefaction, saccharification, fermentation and separation of liquid and solids to produce alcohol and other co-products. Generally, whole cereal, such as corn cereal, is ground to a fine particle size and then mixed with liquid in a slurry tank. The slurry is subjected to high temperatures in a jet cooker along with liquefying enzymes (e.g. alpha-amylases) to solubilize and hydrolyze the starch in the cereal to dextrins. The mixture is cooled down and further treated with saccharifying enzymes (e.g. glucoamylases) to produce fermentable glucose. The mash containing glucose is then fermented for approximately 24 to 120 hours in the presence of ethanol producing microorganisms. The solids in the mash are separated from the liquid phase and ethanol and useful co-products such as distillers' grains are obtained.

Improvements to the above fermentation processes have been accomplished by combining the saccharification step and fermentation step in a process referred to as simultaneous saccharification and fermentation or simultaneous saccharification, yeast propagation and fermentation. These improved fermentation processes have advantages over the previously described dry milling fermentation or even wet milling fermentation processes because significant sugar concentrations do not develop in the fermenter thereby avoiding sugar inhibition of yeast growth. In addition, bacterial growth is reduced due to lack of easily available glucose. Increased ethanol production may result by use of the simultaneous saccharification and fermentation processes.

More recently, fermentation processes have been introduced which eliminate the cooking step or which reduce the need for treating cereal grains at high temperatures. These fermentation processes which are sometimes referred to as no-cook, low temperature or warm cook, include milling of a cereal grain and combining the ground cereal grain with liquid to form a slurry which is then mixed with one or more granular starch hydrolyzing enzymes and optionally yeast at temperatures below the granular starch gelatinization temperature to produce ethanol and other co-products (U.S. Pat. No. 4,514,496, WO 03/066826; WO 04/081193; WO 04/106533; WO 04/080923 and WO 05/069840).

While the above mentioned fermentation processes using a milled grain slurry in combination with granular starch hydrolyzing enzymes offer certain improvements over previous processes, additional fermentation process improvements are needed by the industry for the conversion of granular starch resulting in higher energy efficiency and high end-product production. The object of the present invention is to provide improved processes for the conversion of granular starch into alcohol (e.g. ethanol) and other end products.

SUMMARY OF THE INVENTION

The present invention provides processes for producing an alcohol (e.g. ethanol) from granular starch by contacting the granular starch with an alpha-amylase and providing suitable conditions for endogenous plant hydrolytic enzymes, which hydrolyze solubilized starch to produce glucose. The glucose may then be used as a feedstock in fermentations to produce alcohol.

In one aspect, the invention relates to a process of producing glucose from a granular starch substrate comprising:
  a) contacting a slurry comprising granular starch obtained from plant material with an alpha-amylase at a temperature below the starch gelatinization temperature of the granular starch to produce oligosaccharides and allowing endogenous plant carbohydrate hydrolyzing enzymes to hydrolyze the oligosaccharides, and
  b) producing a mash comprising at least 10% glucose.

In a further embodiment of this aspect, the mash is fermented in the presence of a fermenting microorganism and starch hydrolyzing enzymes at a temperature of between 10° C. and 40° C. for a period of time of 10 hours to 250 hours to produce alcohol, particularly ethanol.

In another aspect, the invention relates to a process for producing ethanol comprising:
  a) contacting a slurry comprising granular starch with an alpha-amylase capable of solubilizing granular starch, wherein said contacting is at a pH of 3.5 to 7.0; at a temperature below the starch gelatinization temperature of the granular starch; and for a period of 5 minutes to 24 hours and obtaining a mash substrate comprising greater than 20% glucose, and
  b) fermenting the substrate in the presence of a fermenting microorganism and a starch hydrolyzing enzyme at a temperature of between 10° C. and 40° C. for a period of 10 hours to 250 hours to produce ethanol.

In further embodiments of either aspect described above, the process includes recovering the ethanol. In yet further embodiments of the described aspects, the process may include additional steps not specified which are performed prior to, during or after the enumerated steps.

DETAILED DESCRIPTION OF THE INVENTION

Figure 1:
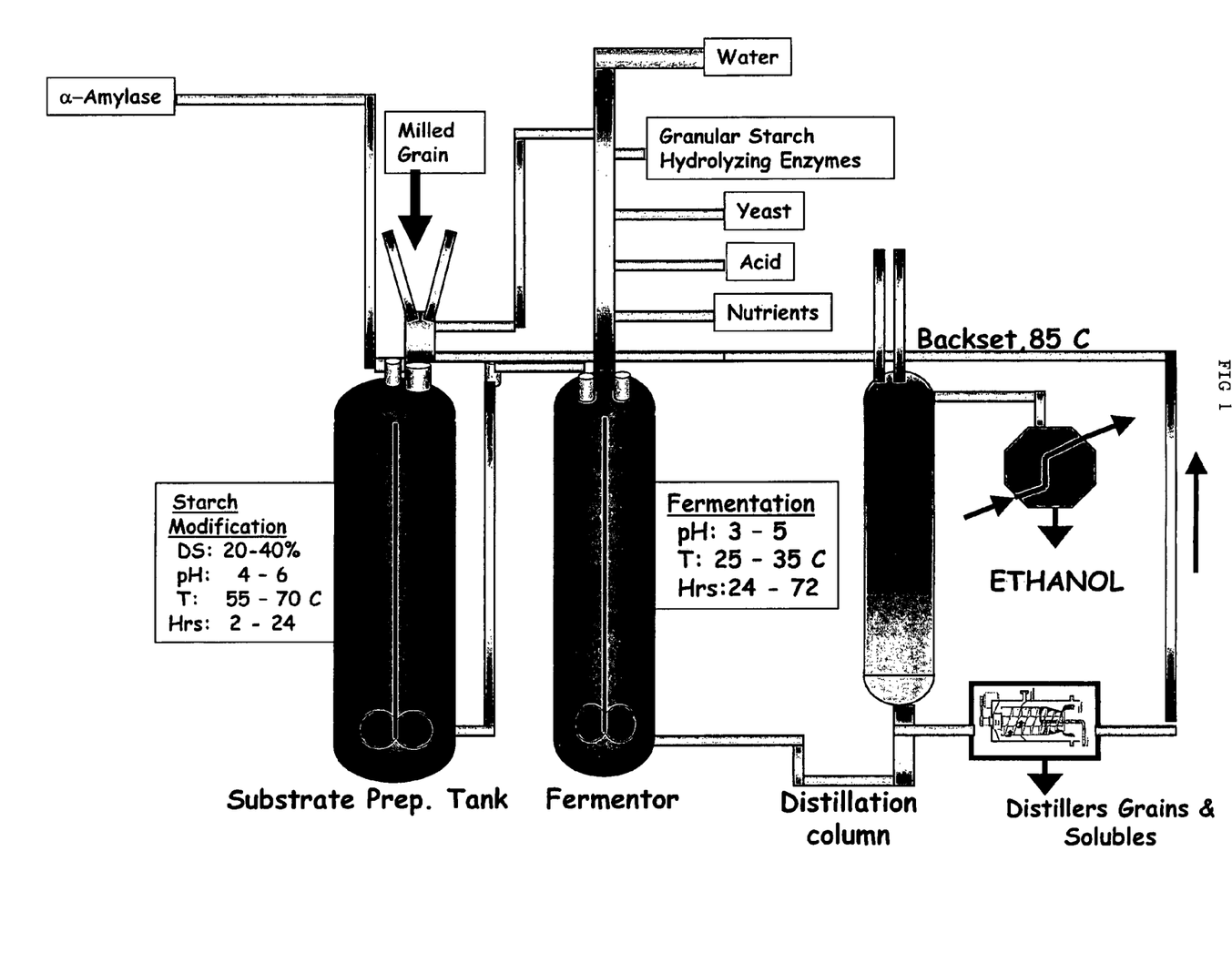
FIG. 1 is a general schematic diagram that illustrates an embodiment of the invention wherein the slurry comprising a milled grain containing granular starch and having a DS of 20 to 40% is contacted with an alpha-amylase at a temperature between 55° C. to 70° C. and a pH of 4.0 to 6.0 for 2 to 24 hours. The resulting mash comprising glucose is transferred to a fermentor and fermented at pH 3.0 to 5.0 at a temperature of 25° C. to 35° C. for 24 to 72 hours in the presence of yeast, nutrients, acid and starch hydrolyzing enzymes to produce ethanol.

Unless defined otherwise herein, all technical and scientific terms used herein have the same meaning as commonly understood by one of ordinary skill in the art to which this invention belongs.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Definitions

The term "fermentation" refers to the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

As used herein the term "starch" refers to any material comprised of the complex polysaccharide carbohydrates of plants, comprised of amylose and amylopectin with the formula $(C_6H_{10}O_5)_x$, wherein x can be any number.

The term "granular starch" refers to raw (uncooked) starch, that is starch in its natural form found in plant material (e.g. grains and tubers).

As used herein the term "dry solids content (DS)" refers to the total solids of a slurry in % on a dry weight basis.

The term "slurry" refers to an aqueous mixture comprising insoluble solids, (e.g. granular starch).

The term "dextrins" refers to short chain polymers of glucose (e.g. 2 to 10 units).

The term "oligosaccharides" refers to any compound having 2 to 10 monosaccharide units joined in glycosidic linkages. These short chain polymers of simple sugars include dextrins.

The term "soluble starch" refers to starch which results from the hydrolysis of insoluble starch (e.g. granular starch).

The term "mash" refers to a mixture of a fermentable substrate in liquid used in the production of a fermented product and is used to refer to any stage of the fermentation from the initial mixing of the fermentable substrate with one or more starch hydrolyzing enzymes and fermenting organisms through the completion of the fermentation run.

The terms "saccharifying enzyme" and "starch hydrolyzing enzymes" refer to any enzyme that is capable of converting starch to mono- or oligosaccharides (e.g. a hexose or pentose).

The terms "granular starch hydrolyzing (GSH) enzyme" and "enzymes having granular starch hydrolyzing (GSH) activity" refer to enzymes, which have the ability to hydrolyze starch in granular form.

The term "hydrolysis of starch" refers to the cleavage of glucosidic bonds with the addition of water molecules.

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units.

The term "gelatinization" means solubilization of a starch molecule by cooking to form a viscous suspension.

The term "gelatinization temperature" refers to the lowest temperature at which gelatinization of a starch containing substrate begins. The exact temperature of gelatinization depends on the specific starch and may vary depending on factors such as plant species and environmental and growth conditions.

The term "below the gelatinization temperature" refers to a temperature that is less than the gelatinization temperature.

The term "glucoamylase" refers to the amyloglucosidase class of enzymes (e.g., E.C.3.2.1.3,glucoamylase, 1,4-alpha-D-glucan glucohydrolase). These are exo-acting enzymes, which release glucosyl residues from the non-reducing ends of amylose and amylopectin molecules. The enzymes also hydrolyzes alpha-1,6 and alpha-1,3 linkages although at much slower rate than alpha-1,4 linkages.

The phrase "simultaneous saccharification and fermentation (SSF)" refers to a process in the production of end products in which a fermenting organism, such as an ethanol producing microorganism, and at least one enzyme, such as a saccharifying enzyme are combined in the same process step in the same vessel.

The term "saccharification" refers to enzymatic conversion of a directly unusable polysaccharide to a mono- or oligosaccharide for fermentative conversion to an end product.

The term "milling" refers to the breakdown of cereal grains to smaller particles. In some embodiments the term is used interchangeably with grinding.

The term "dry milling" refers to the milling of dry whole grain, wherein fractions of the grain such as the germ and bran have not been purposely removed.

The term "liquefaction" refers to the stage in starch conversion in which gelatinized starch is hydrolyzed to give low molecular weight soluble dextrins.

The term "thin-stillage" refers to the resulting liquid portion of a fermentation which contains dissolved material and suspended fine particles and which is separated from the solid portion resulting from the fermentation. Recycled thin-stillage in industrial fermentation processes is frequently referred to as "back-set".

The term "vessel" includes but is not limited to tanks, vats, bottles, flasks, bags, bioreactors and the like. In one embodiment, the term refers to any receptacle suitable for conducting the saccharification and/or fermentation processes encompassed by the invention.

The term "end product" refers to any carbon-source derived product which is enzymatically converted from a fermentable substrate. In some preferred embodiments, the end product is an alcohol, such as ethanol.

As used herein the term "fermenting organism" refers to any microorganism or cell which is suitable for use in fermentation for directly or indirectly producing an end product.

As used herein the term "ethanol producer" or ethanol producing microorganism" refers to a fermenting organism that is capable of producing ethanol from a mono- or oligosaccharide.

The term "derived" encompasses the terms "originated from", "obtained" or "obtainable from", and "isolated from" and in some embodiments as used herein means that a polypeptide encoded by the nucleotide sequence is produced from a cell in which the nucleotide is naturally present or in which the nucleotide has been inserted.

The term "heterologous" with reference to a protein or polynucleotide refers to a protein or polynucleotide that does not naturally occur in a host cell.

The term "endogenous" with reference to a protein or polynucleotide refers to a protein or polynucleotide that does naturally occur in a host cell.

The phrase "endogenous plant hydrolytic enzymes capable of hydrolyzing soluble starch" refers to hydrolytic enzymes that are expressed and produced in a plant and may be produced by the expression of endogenous or heterologous genes.

The term "enzymatic conversion" in general refers to the modification of a substrate by enzyme action. The term as used herein also refers to the modification of a fermentable substrate, such as a granular starch containing substrate by the action of an enzyme.

The terms "recovered", "isolated", and "separated" as used herein refer to a compound, protein, cell, nucleic acid or amino acid that is removed from at least one component with which it is naturally associated.

As used herein the term "enzyme unit" refers to the amount of enzyme that produces 1 micromole of product per minute under the specified conditions of the assay. For example, in one embodiment, the term "glucoamylase activity unit" (GAU) is defined as the amount of enzyme required to produce 1 g of glucose per hour from soluble starch substrate (4% DS) under assay conditions of 60° C. and pH 4.2.

The term "yield" refers to the amount of end product produced using the methods of the present invention. In some embodiments, the term refers to the volume of the end product and in other embodiments, the term refers to the concentration of the end product.

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100. An instructive method for determining the DE of a slurry or solution is described in Schroorl's method (Fehling's assay titration).

As used herein the term "comprising" and its cognates are used in their inclusive sense; that is, equivalent to the term "including" and its corresponding cognates.

"A", "an" and "the" include plural references unless the context clearly dictates otherwise.

Numeric ranges are inclusive of the numbers defining the range.

The headings provided herein are not limitations of the various aspects or embodiments of the invention, which can be had by reference to the specification as a whole.

Embodiments of the Invention (A) Raw Materials:
Granular Starch—

Granular starch may be obtained from plant material including but not limited to wheat, corn, rye, sorghum (milo), rice, millet, barley, triticale, cassava (tapioca), potato, sweet potato, sugar beets, sugarcane, and legumes such as soybean and peas. Preferred plant material includes corn, barley, wheat, rice, milo and combinations thereof. Particularly preferred plant material is obtained from corn (*Zea mays*). Plant material may include hybrid varieties and genetically modified varieties (e.g. transgenic corn, barley or soybeans comprising heterologous genes). Any part of the plant may be used to provide granular starch including but not limited to plant parts such as leaves, stems, hulls, husks, tubers, cobs, grains and the like. In some embodiments, essentially the entire plant may be used, for example, the entire corn stover may be used. In one embodiment, whole grain may be used as a source of granular starch. Preferred whole grains include corn, wheat, rye, barley, sorghum and combinations thereof. In other embodiments, granular starch may be obtained from fractionated cereal grains including fiber, endosperm and/or germ components. Methods for fractionating plant material such as corn and wheat are known in the art. In some embodiments, plant material obtained from different sources may be mixed together to obtain granular starch used in the processes of the invention (e.g. corn and milo or corn and barley).

In some embodiments, plant material comprising granular starch may be prepared by means such as milling. In particular, means of milling whole cereal grains are well known and include the use of hammer mills and roller mills.

Alpha-Amylases—

In some of the embodiments encompassed by the invention, the alpha-amylase is a microbial enzyme having an E.C. number, E.C. 3.2.1.1-3 and in particular E.C. 3.2.1.1. Any suitable alpha-amylase may be used in the present process. In some embodiments, the alpha-amylase is derived from a bacterial strain and in other embodiments the alpha-amylase is derived from a fungal strain. In further embodiments, the preferred alpha-amylase is a bacterial alpha-amylase. In other embodiments, the alpha-amylase is an acid stable alpha-amylase. Suitable alpha-amylases may be naturally occurring as well as recombinant (hybrid and variants) and mutant alpha-amylases (WO 99/19467 and WO 97/41213). In particularly preferred embodiments, the alpha-amylase is derived from a *Bacillus* species. Preferred *Bacillus* species include *B. subtilis, B. stearothermophilus, B. lentus, B. licheniformis, B. coagulans,*and *B. amyloliquefaciens* (U.S. Pat. Nos. 5,093,257; 5,763,385; 5,824,532; 5,958,739; 6,008,026, 6,361,809; 6,867,031; WO 96/23874; WO 96/39528 and WO 05/001064). Particularly preferred alpha-amylases are derived from *Bacillus* strains *B. stearothermophilus, B. amyloliquefaciens* and *B. licheniformis* ((U.S. Pat. Nos. 6,187,576; 6,093,562; 5,958,739; US 2006/0014265 and WO 99/19467).

Most preferred alpha-amylases are amylases derived from *B. stearothermophilus* and *B. licheniformis* including wild-type, hybrid and variant alpha-amylase enzymes. See Suzuki et al., (1989) J. Biol. Chem. 264:18933-18938 and US 2006/0014265,particularly SEQ ID NOs: 3, 4 and 16.Reference is also made to strains having American Type Culture Collection (ATCC) numbers—ATCC 39709; ATCC 11945; ATCC 6598; ATCC 6634; ATCC 8480; ATCC 9945 and NCIB 8059.

In addition to the bacterial alpha-amylases, fugal alpha-amylases are contemplated for use in the processes of the invention. Suitable fungal alpha-amylases are derived from filamentous fungal strains such as *Aspergillus*, such as *A. oryzae* and *A. niger* (e.g. FUNGAMYL and CLARASE L), and *Trichoderma, Rhizopus, Mucor,* and *Penicillium.*

Commercially available alpha-amylases contemplated for use in the methods of the invention include; SPEZYME AA; SPEZYME FRED; SPEZYME ETHYL; GZYME G997; CLARASE L (Genencor International Inc.); TERMAMYL 120-L, LC, SC and SUPRA (Novozymes Biotech); LIQUOZYME X and SAN SUPER (Novozymes A/S) and ULTRA THIN (Nalley Research).

Plant Enzymes—

Plants have naturally occurring starch degrading enzymes such as alpha-amylases (EC 3.1.1.1); beta-amylases (EC 3.1.1.2), amyloglucosidases (glucoamylase) (EC 3.1.1.3) and starch phosphorylases (EC 2.4.1.1). In addition, plants may have been genetically engineered to include heterologous genes encoding starch degrading enzymes, such as amylases, glucoamylase and others (WO 03/018766 and WO 05/096804). Endogenous starch degrading plant enzymes, whether naturally occurring or expressed from an introduced polynucleotide, with exposure to elevated temperatures, such as the temperatures of jet cooking or even temperatures above the gelatinization temperature of granular starch will become inactivated. However, at temperatures conducted in the present process, it is believed that the endogenous starch degrading enzymes are not inactivated and actually contribute to the hydrolysis of granular starch. Although not bound to theory, the inventors believe that the alpha-amylase provided in the contacting step modifies the granular starch structure of the plant material allowing for the production of oligosaccharides including dextrins. The oligosaccharides are further degraded at the temperatures encompassed by the contacting step (e.g. 45° C. to 70° C.) by plant starch degrading enzymes. The plant starch degrading enzymes act on the partially hydrolyzed starch to produce glucose. While exogenous sources of glucoamylases may be included in the contacting step, the addition of exogenous glucoamylase is not required to provide glucose, which is then optionally used as a feedstock for alcohol fermentation. Therefore in one embodiment, the contacting step of the invention does not include the addition of glucoamylases derived from microbial sources. However, the addition of glucoamylases and/or other enzymes such as phytases and proteases may increase the production of solubilized granular starch.

Fermenting Organisms—

Examples of fermenting organisms are ethanologenic microorganisms or ethanol producing microorganisms such as ethanologenic bacteria which express alcohol dehydrogenase and pyruvate dehydrogenase and which can be obtained from *Zymomonas moblis* (See e.g. U.S. Pat. Nos. 5,000,000; 5,028,539, 5,424,202; 5,514,583 and 5,554,520). In additional embodiments, the ethanologenic microorganisms express xylose reductase and xylitol dehydrogenase, enzymes that convert xylose to xylulose. In further embodiments, xylose isomerase is used to convert xylose to xylulose. In particularly preferred embodiments, a microorganism capable of fermenting both pentoses and hexoses to ethanol are utilized. For example, in some embodiments the microorganism may be a natural or non-genetically engineered microorganism or in other embodiments the microorganism may be a recombinant microorganism. For example, in some embodiments the preferred fermenting microorganisms include bacterial strains from *Bacillus, Lactobacillus, E. coli, Erwinia, Pantoea* (e.g., *P. citrea*) and *Klebsiella* (e.g. *K. oxytoca*). (See e.g. U.S. Pat. Nos. 5,028,539, 5,424,202 and WO 95/13362).

In further preferred embodiments, the ethanol-producing microorganism is a fungal microorganism, such as a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China).

Secondary Enzymes—

While in one embodiment, it is contemplated that additional starch hydrolyzing enzymes are not needed, and therefore not included in the contacting step, additional enzymes may be included in both the contacting step and fermenting step encompassed by the invention. In some embodiments, these enzymes will be included as a secondary enzyme in the contacting step, which comprises contacting the granular starch slurry with an alpha-amylase and one or more secondary enzymes. In other embodiments, the additional enzymes will be included in the fermentation step along with yeast and other components.

In some embodiments during the contacting step with the alpha-amylase, the secondary enzyme may include a glucoamylase, granular starch hydrolyzing enzymes, a protease, a phytase, a cellulase, a hemicellulases, a pullulanase, a xylanase, a lipase, a cutinase, a pectinase, a beta-glucanase, a beta amylase, a cyclodextrin transglycosyltransferase and combinations thereof In some preferred embodiments, the contacting step will include a combination of an alpha-amylase, a phytase and optionally a protease. In other embodiments, the contacting step will include a combination of an alpha-amylase, a glucoamylase and optionally a protease. In yet other embodiments, the contacting step will include a combination of an alpha-amylase, a glucoamylase, a phytase and optionally a protease.

Glucoamylases (GA) (E.C. 3.2.1.3.) may be derived from the heterologous or endogenous protein expression of bacteria, plants and fungi sources. Preferred glucoamylases useful in the compositions and methods of the invention are produced by several strains of filamentous fungi and yeast. In particular, glucoamylases secreted from strains of *Aspergillus* and *Trichoderma* are commercially important. Suitable glucoamylases include naturally occurring wild-type glucoamylases as well as variant and genetically engineered mutant glucoamylases. The following glucoamylases are nonlimiting examples of glucoamylases that may be used in the process encompassed by the invention. *Aspergillus niger* G1 and G2 glucoamylase (Boel et al., (1984) EMBO J. 3:1097-1102; WO 92/00381, WO 00/04136 and U.S. Pat. No. 6,352,851); *Aspergillus awamori* glucoamylases (WO 84/02921); *Aspergillus oryzae* glucoamylases (Hata et al., (1991) Agric. Biol. Chem. 55:941-949) and *Aspergillus shirousami*. (See Chen et al., (1996) Prot. Eng. 9:499-505; Chen et al. (1995) Prot. Eng. 8:575-582; and Chen et al., (1994) Biochem J. 302:275-281).

Glucoamylases are also obtained from strains of *Talaromyces* such as those derived from *T. emersonii, T. leycettanus, T. duponti* and *T. thermophilus* (WO 99/28488; U.S. Pat. No. RE: 32,153; U.S. Pat. No. 4,587,215); strains of *Trichoderma*, such as *T. reesei T reesei* and particularly glucoamylases having at least 80%, 85%, 90% and 95% sequence identity to SEQ ID NO: 4 disclosed in US Pat. Pub. No. 2006-0094080; strains of *Rhizopus*, such as *R. niveus* and *R. oryzae*; strains of *Mucor* and strains of *Humicola*, such as *H. grisea* (See, Boel et al., (1984) EMBO J. 3:1097-1102; WO 92/00381; WO 00/04136; Chen et al., (1996) Prot. Eng. 9:499-505; Taylor et al., (1978) Carbohydrate Res. 61:301-308; U.S. Pat. Nos. 4,514,496; 4,092,434; and Jensen et al., (1988) Can. J. Microbiol. 34:218-223). Other glucoamylases useful in the present invention include those obtained from *Athelia rolfsii* and variants thereof (WO 04/111218).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) J. Biochem. 98:663-671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Also the enzyme preparation GC480 (Genencor International Inc.) finds use in the invention.

Granular starch hydrolyzing enzymes (GSHEs) are able to hydrolyze granular starch, and these enzymes have been recovered from fungal, bacterial and plant cells such as *Bacillus* sp., *Penicillium* sp., *Humicola* sp., *Trichoderma* sp. *Aspergillus* sp. *Mucor* sp. and *Rhizopus* sp. In one embodiment, a particular group of enzymes having GSH activity include enzymes having glucoamylase activity and/or alpha-amylase activity (See, Tosi et al., (1993) Can. J. Microbiol. 39:846-855). A *Rhizopus oryzae* GSHE has been described in Ashikari et al., (1986) Agric. Biol. Chem. 50:957-964 and U.S. Pat. No. 4,863,864. *A Humicola grisea* GSHE has been described in Allison et al., (1992) Curr. Genet. 21:225-229; WO 05/052148 and European Patent No. 171218. An *Aspergillus awamori* var. *Kawachi* GSHE has been described by Hayashida et al., (1989) Agric. Biol. Chem 53:923-929. An *Aspergillus shirousami* GSHE has been described by Shibuya et al., (1990) Agric. Biol. Chem. 54:1905-1914.

In one embodiment, a GSHE may have glucoamylase activity and is derived from a strain of *Humicola grisea*, particularly a strain of *Humicola grisea* var. *thermoidea* (see, U.S. Pat. No. 4,618,579). In some preferred embodiments, the Humicola enzyme having GSH activity will have at least 85%, 90%, 92%, 94%, 95%, 96%, 97%, 98% and 99% sequence identity to the amino acid sequence of SEQ ID NO: 3 of WO 05/052148.

In another embodiment, a GSHE may have glucoamylase activity and is derived from a strain of *Aspergillus awamori*, particularly a strain of *A. awamori* var. *kawachi*. In some preferred embodiments, the *A. awamori* var. *kawachi* enzyme having GSH activity will have at least 85%, 90%, 92%, 94%, 95%, 96%, 97%, 98% and 99% sequence identity to the amino acid sequence of SEQ ID NO: 6 of WO 05/052148.

In another embodiment, a GSHE may have glucoamylase activity and is derived from a strain of *Rhizopus*,such as *R. niveus* or *R. oryzae*. The enzyme derived from the Koji strain *R. niveus* is sold under the trade name "CU CONC or the enzyme from *Rhizopus* sold under the trade name GLUZYME.

Another useful GSHE having glucoamylase activity is SPIRIZYME Plus (Novozymes A/S), which also includes acid fungal amylase activity.

In another embodiment, a GSHE may have alpha-amylase activity and is derived from a strain of *Aspergillus* such as a strain of *A. awamori*, *A. niger*, *A. oryzae*, or *A. kawachi* and particularly a strain of *A. kawachi*.

In some preferred embodiments, the *A. kawachi* enzyme having GSH activity will have at least 85%, 90%, 92%, 94%, 95%, 96%, 97%, 98% and 99% sequence identity to the amino acid sequence of SEQ ID NO: 3 of WO 05/118800 and WO 05/003311.

In some embodiments, the enzyme having GSH activity is a hybrid enzyme, for example one containing a catalytic domain of an alpha-amylase such as a catalytic domain of an *Aspergillus niger* alpha-amylase, an *Aspergillus oryzae* alpha-amylase or an *Aspergillus kawachi* alpha-amylase and a starch binding domain of a different fungal alpha-amylase or glucoamylase, such as an *Aspergillus kawachi* or a *Humicola grisea* starch binding domain. In other embodiments, the hybrid enzyme having GSH activity may include a catalytic domain of a glucoamylase, such as a catalytic domain of an *Aspergillus* sp., a *Talaromyces* sp., an *Althea* sp., a *Trichoderma* sp. or a *Rhizopus* sp. and a starch binding domain of a different glucoamylase or an alpha-amylase. Some hybrid enzymes having GSH activity are disclosed in WO 05/003311, WO 05/045018; Shibuya et al., (1992) Biosci. Biotech. Biochem 56: 1674-1675 and Cornett et al., (2003) Protein Engineering 16:521-520.

Suitable proteases include microbial proteases, such as fungal and bacterial proteases, for example, acid fungal proteases such as NSP24 and also GC106 (Genencor International Inc.). Preferred fungal proteases are derived from strains of *Aspergillus* (e.g. proteases from *A. niger* and *A. oryzae*), *Mucor* (e.g. *M. miehei*), *Trichoderma*, *Rhizopus*,and *Candida*. Preferred bacterial proteases are derived from strains of *Bacillus* such as *B. amyloliquefaciens*.Proteases added to the fermentation may increase the free amino nitrogen level and increase the rate of metabolism of the yeast and further give higher fermentation efficiency.

Enzymes that may be used in the methods of the invention include beta-amylases (E.C. 3.2.1.2). These are exo-acting maltogenic amylases, which catalyze the hydrolysis of 1,4-alpha-glucosidic linkages in amylose, amylopectin and related glucose polymers. Commercial beta-amylases are available from Genencor International Inc., and examples include SPEZYME BBA and OPTIMALT BBA.

Cellulases (E.C. 3.2.1.4) such as endo-glucanases may be used in the methods of the invention. Examples of cellulases include cellulases from filamentous fungus such as *Trichoderma*, *Humicola*, *Fusarium*,and *Aspergillus*. Commercially cellulases are available as SPEZYME CP and LAMINEX (Genencor International, Inc) and CELLUZYME and ULTRAFLO (Novozymes A/S).

Xylanases useful in the methods of the invention may be from bacterial or fungal sources, such as *Aspergillus*, *Trichoderma*, *Neurospora*, and *Fusarium*. Commercial preparations include SPEZYME CP and LAMINEX (Genencor International, Inc.) and ULTRAFLO (Novozymes A/S).

A number of bacterial and fungal phytases (E.C. 3.1.3.8 and 3.1.3.26) are known and in some embodiments the addition of phytases are particularly useful in the methods. Yeast phytases may be derived from strains of *Saccharomyces* (e.g. *S. cerevisiae*) and *Schwanniomyces* (e.g. *S. occidentalis*) (Wodzinski et al., Adv. Apple. Microbiol., 42:263-303). Other fungal phytases have been described in the literature and reference is made to Wyss et al., (1999) Appl. Environ Microbiol. 65:367-373; Berka et al., (1998) Appl. Environ. Microbiol. 64: 4423-4427; Yamada et al., (1986) Agric. Biol. Chem. 322:1275-1282; PCT Publication Nos. WO 98/28408; WO 98/28409; WO 97/38096 and WO 9844125; and U.S. Pat. Nos. 6,734,004; 6,350,602; and 5,863,533). Fungal phytases have been derived from *Aspergillus* (e.g. *A. niger*, *A. awamori*, *A. terreus*, *A. oryzea* and *A. fumigatus*); *Thermomyces (Humicola) lanuginousus*; *Fusarium* (*F. javanicum* and *F. versillibodes*). Bacterial phytases may also find use in the invention (Greiner R. et al. (1993) Arch. Biochem. Biophys. 303: 107-113; Yoon S. J. et al. (1996) Enzyme and Microbial Technol. 18: 449-454; and WO 06/043178).

Commercially available phytases which may be used according to the invention include PHYZYME XP 5000 (Danisco A/S); FINASE (Altech); GC 491; FINASE, SPEZYME HPA (Genencor), BIO-FEED PHYTASE and PHYTASE NOVO (Novozymes) and NATUPHOS (DSM).

One skilled in the art can readily determine the effective amount of the enzymes which may be used in the process steps encompassed by the invention.

(B) Process Steps—

The granular starch (e.g. milled cereal grain) to be processed is mixed with an aqueous solution to obtain a slurry. The aqueous solution may be obtained, for example from water, thin stillage and/or backset.

A slurry may have a DS of between 5-60%; 10-50%; 15-45%; 15-30%; 20-45%; 20-30% and also 25-40%. The contacting step with an alpha-amylase is conducted at a pH range of 3.5 to 7.0;also at a pH range of 3.5 to 6.5;preferably at a pH range of 4.0 to 6.0 and more preferably at a pH range of 4.5 to 5.5.The slurry is held in contact with the alpha-amylase at a temperature below the starch gelatinization temperature of the granular starch. In some embodiments, this temperature is held between 45° C. and 70° C.; in other embodiments, the temperature is held between 50° C. and 70° C.; between 55° C. and 70° C.; between 60° C. and 70° C., between 60° C. and 65° C.; between 55° C. and 65° C. and between 55° C. and 68° C. In further embodiments, the temperature is at least 45° C., 48° C., 50° C., 53° C., 55° C., 58° C., 60° C., 63° C., 65° C. and 68° C. In other embodiments, the temperature is not greater than 65° C., 68° C., 70° C., 73° C., 75° C. and 80° C.

The initial starch gelatinization temperature ranges for a number of granular starches which may be used in accordance with the processes herein include barley (52° C. to 59° C.), wheat (58° C. to 64° C.), rye (57° C. to 70° C.), corn (62° C. to 72° C.), high amylose corn (67° C. to 80° C.), rice (68° C. to 77° C.), sorghum (68° C. to 77° C.), potato (58° C. to 68° C.), tapioca (59° C. to 69° C.) and sweet potato (58° C. to 72° C.). (J. J. M. Swinkels pg 32-38 in STARCH CONVERSION TECHNOLOGY, Eds Van Beynum et al., (1985) Marcel Dekker Inc. New York and The Alcohol Textbook $3^{rd}$ ED. A Reference for the Beverage, Fuel and Industrial Alcohol Industries, Eds Jacques et al., (1999) Nottingham University Press, UK).

In the contacting step, the slurry may be held in contact with the alpha-amylase for a period of 5 minutes to 48 hours; and also for a period of 5 minutes to 24 hours. In some embodiments the period of time is between 15 minutes and 12 hours, 15 minutes and 6 hours, 15 minutes and 4 hours and also 30 minutes and 2 hours.

The effective concentration of the alpha-amylase used in the contacting step will vary according to the specific process conditions and granular starch used. However, in general the amount of alpha-amylase used will be in the range of 0.001 to 50 AAU/g DS, 0.01 to 30 AAU/g DS, 0.01 to 10 AAU/g DS and also 0.05 to 5.0 AAU/g DS.

In some embodiments, the effective dose of an alpha-amylase in the contacting step and/or fermentation step will be 0.01 to 15 SSU/g DS; also 0.05 to 10 SSU/g DS; also 0.1 to 10 SSU/g DS; and 0.5 to 5 SSU/g DS.

In some embodiments, the effective dose of a glucoamylase for the contacting step and/or the fermentation step will be in the range of 0.01 to 15 GAU/g DS; also 0.05 to 10 GAU/g DS; also 0.1 to 10 GAU/g DS and even 0.5 to 5 GAU/g DS.

In some embodiments, the effective dose of a phytase to be used in the contacting step and/or fermentation step will be in the range of 0.001 to 15 FTU/g DS; also 0.005 to 10 FTU/g DS; and also 0.05 to 5 FTU/g DS. One phytase unit (FTU) is the amount of enzyme, which liberates 1 micromole inorganic phosphorus per minute from sodium phytate, 0.0051 moles/liter, at 37° C. and at pH 5.0.

In some embodiments, the effective dose of a protease to be used in the contacting step and/or fermentation step will be in the range of 0.01 to 15 SAPU/g DS; also 0.01 to 10 SAPU/g DS; and also 0.05 to 5 SAPU/g DS. SAPU refers a spectrophotometric acid protease unit, wherein 1 SAPU is the amount of protease enzyme activity that liberates one micromole of tyrosine per minute from a casein substrate under conditions of the assay.

During the contacting step between 25-90% of the granular starch is solubilized to produce oligosaccharides comprising dextrin. In some embodiments, greater than 20%, 25%, 30%, 35%, 40%, 45%, 50%, 55%, 60%, 65%, 70%, 75%, 80%, 85% and 90% of the granular starch is solubilized.

After contacting the granular starch with the alpha-amylase for a period of time as indicated above, a soluble starch substrate (mash) is obtained which comprises greater than 10%, 15%, 20%, 25%, 30%, 35%, 40%, 45%, 50%, 55%, 60%, 65%, 70%, 75% and 80% glucose.

In some preferred embodiments of the contacting step, a slurry comprising granular corn starch having a DS of 20-40% is contacted with an alpha-amylase derived from *Bacillus stearothermophilus* or *Bacillus licheniformis* for 1 to 6 hours at a temperature between 55° C. to 70° C. to obtain a soluble starch substrate comprising at least 30% glucose. In other preferred embodiments of the contacting step, a slurry comprising granular milo starch having a DS of 20-40% is contacted with an alpha-amylase derived from *Bacillus stearothermophilus* or *Bacillus licheniformis* for 1 to 6 hours at a temperature between 55° C. to 70° C. to obtain a soluble starch substrate comprising at least 50% glucose.

After the contacting step which results in the production of a mash comprising glucose, the mash is subjected to fermentation with a fermenting microorganism (e.g. an ethanol-producing microorganism).

However, prior to subjecting the mash including at least 10% glucose to fermentation, the mash may be further exposed to an aqueous solution comprising, for example backset and/or corn steep and adjusted to a pH in the range of pH 3.0 to 6.0;pH 3.5 to 5.5, or pH 4.0 to 5.5. In this embodiment of the invention, the % DS of the mash may be diluted. For example, the DS of the diluted mash maybe between 5 to 35%; 5 to 30%; 5 to 25%; 5 to 20%; 5 to 20%; 5 to 15%; and 5 to 10% less than the % DS of the slurry in the contacting step. In one non-limiting example, if the % DS of the slurry in the contacting step is approximately 32% and the mash is further exposed to a diluting aqueous solution which dilutes the DS between 5 to 10%, the DS of the mash to be fermented will be between 22% and 27%. In some preferred embodiments, if the DS of the contacting slurry is between 30 to 35%, the DS of the diluted slurry will be about 20 to 30%.

In a preferred embodiment, the mash comprising at least 10% glucose is then subjected to fermentation processes using fermenting microorganisms as described above. These fermentation processes are described in The Alcohol Textbook $3^{rd}$ ED, A Reference for the Beverage, Fuel and Industrial Alcohol Industries, Eds Jacques et al., (1999) Nottingham University Press, UK.

In some preferred embodiments, the mash is fermented with a yeast at temperatures in the range of 15 to 40° C. and also 25 to 35° C.; at a pH range of pH 3.0 to 6.5; also pH 3.0 to 6.0; pH 3.0 to 5.5, pH 3.5 to 5.0 and also pH 3.5 to 4.5 for a period of time of 12 to 240 hours, preferably 12 to 120 and more preferably from 24 to 90 hours to produce an alcohol product, preferably ethanol.

Yeast cells are generally supplied in amounts of $10^4$ to $10^{12}$, and preferably from $10^7$ to $10^{10}$ viable yeast count per ml of fermentation broth. The fermentation will include in addition to a fermenting microorganisms (e.g. yeast) nutrients, optionally acid and additional enzymes.

In one preferred embodiment, the contacting step is conducted in a separate vessel from the fermenting step. It is also contemplated that the contacting step and fermenting step may be conducted in a SSF process in the same vessel.

In some embodiments, in addition to the raw materials described above, fermentation media will contain supplements including but not limited to vitamins (e.g. biotin, folic acid, nicotinic acid, riboflavin), cofactors, and macro and micro-nutrients and salts (e.g. $(NH4)_2SO_4$; $K_2HPO_4$; NaCl; $MgSO_4$; $H_3BO_3$; $ZnCl_2$; and $CaCl_2$).

Additional enzymes to be included in the fermentation step may be the same or different from the enzymes used in the contacting step. In some embodiments, the enzyme will include alpha-amylases and glucoamylases, including granular starch hydrolyzing enzymes. In some preferred embodiments, the glucoamylase and alpha-amylase may occur in a blend. Particularly preferred enzyme blends include STARGEN 001 (Genencor International Inc.), which is a blend of an alpha-amylase from *A. kawachi* and a glucoamylase from *A. niger*. In some preferred embodiments, the glucoamylase will be derived from a *Trichoderma reesei* glucoamylase, a *Athelia rolfi* glucoamylase, a Talaromyces glucoamylase, a *Aspergillus* glucoamylase and hybrid and variants glucoamylase derived there from. In some preferred embodiments, the enzyme is selected from a cellulase, a phytase and a protease.

Recovery of Alcohol and Other End Products—

The preferred end product of the instant fermentation process is an alcohol product, preferably ethanol. The end product produced according to the process may be separated and/or purified from the fermentation media. Methods for separation and purification are known, for example by subjecting the media to extraction, distillation and column chromatography. In some embodiments, the end product is identified directly by submitting the media to high-pressure liquid chromatography (HPLC) analysis.

In further embodiments, the mash may be separated by for example centrifugation into the liquid phase and solids phase and end products such as alcohol and solids recovered. The alcohol may be recovered by means such as distillation and molecular sieve dehydration or ultra filtration.

In some embodiments, the yield of ethanol will be greater than 8%, 10%, 12%, 14%, 16% and 18% by volume. The ethanol obtained according to process of the invention may be used as a fuel ethanol, potable ethanol or industrial ethanol.

In further embodiments, the end product may include the fermentation co-products such as distillers dried grains (DDG) and distiller's dried grain plus solubles (DDGS), which may be used as an animal feed.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply: GA (glucoamylase); wt % (weight percent); ° C. (degrees Centigrade); $H_2O$ (water); $dH_2O$ (deionized water); $dIH_2O$ (deionized water, Milli-Q filtration); g or gm (grams); μg (micrograms); mg (milligrams); kg (kilograms); μL (microliters); ml and mL (milliliters); mm (millimeters); μm (micrometer); M (molar); mM (millimolar); μM (micromolar); U (units); MW (molecular weight); sec (seconds); min(s) (minute/minutes); hr(s) (hour/hours); DO (dissolved oxygen); WNV (weight to volume); W/W (weight to weight); VN (volume to volume); Genencor (Genencor International, Inc., Palo Alto, Calif.); MT (Metric ton); and ETOH (ethanol).

The following enzyme preparations were used in the examples below:

SPEZYME Ethyl (available from Genencor)—a bacterial alpha-amylase obtained from a genetically modified strain of *Bacillus licheniformis*.

GC100—an experimental bacterial alpha-amylase disclosed in US 2006/0014265.

*Humicola grisea* glucoamylase (HGA) having the amino acid sequence disclosed as SEQ ID NO: 3 of WO 2005/052148.

STARGEN 001 (available from Genencor)—a blend of *Aspergillus niger* glucoamylase and *Aspergillus kawachi* alpha-amylase.

The following assays were used in the examples below:

The activity of alpha-amylase is expressed as alpha amylase units (AAU) and enzyme activity was determined by the rate of starch hydrolysis, as reflected in the rate of decrease of iodine-staining capacity, which was measured spectrophotometrically. One AAU of bacterial alpha-amylase activity is the amount of enzyme required to hydrolyze 10 mg of starch per min under standardized conditions.

Alpha-amylase activity made also determined as soluble starch unit (SSU) and is based on the degree of hydrolysis of soluble potato starch substrate (4% DS) by an aliquot of the enzyme sample at pH 4.5, 50° C. The reducing sugar content is measured using the DNS method as described in Miller, G. L. (1959) Anal. Chem. 31:426-428. One unit of the enzyme activity (SSU) is equivalent to the reducing power of 1 mg of glucose released per minute at the specific incubation conditions.

Glucoamylase activity was measured using a well-known assay which is based on the ability of glucoamylase to catalyze the hydrolysis of p-nitrophenyl-alpha-D-glucopyranoside (PNPG) to glucose and p-nitrophenol. At an alkaline pH, the nitrophenol; forms a yellow color that is proportional to glucoamylase activity and is monitored at 400 nm and compared against an enzyme standard measured as a GAU.

One "Glucoamylase Activity Unit" (GAU) is the amount of enzyme that will produce 1 gm of reducing sugar, calculated as glucose per hour from a soluble starch substrate (4% DS) at pH 4.2 and 60° C.

Brix, the measurement of total solubilized solid content at a given temperature was determined by measurement with a Refractometer.

Determination of total starch content: The enzyme-enzyme starch liquefaction and saccharification process was used to determine the total starch content. In a typical analysis, 2 g of dry sample was taken in a 100 ml Kohlraucsh flask and 45 ml of MOPS buffer, pH 7.0 was added. The slurry was well stirred for 30 min. SPEZYME FRED (1:50 diluted in water) (Genencor), 1.0 ml was added and heated to boiling for 3-5 min. The flask was placed in an autoclave maintained at 121° C. for 15 min. After autoclaving the flask was placed in a water bath at 95° C. and 1 ml of 1:50 diluted SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX L-400 (Genencor) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

Determination of the % solubilized solids—a 7 ml sample was placed in a small screw cap test tube (pH adjusted to 5.0 to 6.0) and 0.007 ml SPEZYME Fred was added to the tube. The test tube was placed in a boiling water bath for 10 min and gently mixed at various times during the incubation. After 10 min the tube was removed and placed in a 80° C. water bath for 1 hr. The tube was cooled and centrifuges. The Brix of the supernatant was determined and compared to a control sample. The % solubilized solids=control Brix×100/sample Brix.

Ethanol and carbohydrate determinations of the samples were determined using the HPLC method as follows:

a 1.5 mL Eppendorf centrifuge tube was filled with fermentor mash and cooled on ice for 10 min; the sample tube was centrifuged for 1 min in an Eppendorf table top centrifuge; a 0.5 mL sample of the supernatant was transferred to a test tube containing 0.05 mL of 1.1N $H_2SO_4$ and allowed to stand for 5 min; 5.0 mL of water was added to the test tube and then the sample was filtered into a HPLC vial through 0.2 μm Nylon Syringe Filter; and run on HPLC. The HPLC conditions included:

Ethanol System: Column: Phenomenex Rezex Organic Acid Column (RHM-Monosaccharide) #00H 0132-KO (Equivalent to Bio-Rad 87H); Column Temperature: 60° C.; Mobile Phase: 0.01 N $H_2SO_4$; Flow Rate: 0.6 mL/min; Detector: RI; and Injection Volume: 20 μL.

Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min; Detector: RI; Injection Volume: 10 μL (3% DS material).

The column separated based on the molecular weight of the saccharides, which are designated as DP1 (glucose); DP2 (disaccharides); DP3 (trisaccharides) and DP>3 (oligosaccharide sugars having a degree of polymerization greater than 3).

EXAMPLE 1

Solubilization and Ethanol Production From Granular Starch of Whole Ground Corn and Fractionated Corn This experiment was run on three different corn granular starch substrates (A) 370 g of whole ground corn having a moisture content of 13.3%; (B) 354.2 g corn endosperm having a moisture content of 9.2%; and (C) refined corn starch obtained from having a moisture content of 11.8%. Each substrate was weighed and transferred to a stainless steel vessel to make a final 1000 g slurry with water corresponding to 32% DS.

The pH of the slurry was adjusted to pH 5.5 using 6N $H_2SO_4$. GC100 (4.0AAU/g DS) was added. The temperature was maintained at 60° C. During the incubation the slurry was gently stirred with an overhead mixer. After time internals of 2, 4, 6, 12 and 24 hours, the BRIX, % solubilized starch and sugar compositions (% W/W) were determined, and the results are illustrated in Table 1. At 24 hours, 79.1%, 71.1% and 60.0% of the granular starch from whole ground corn, endosperm and refined sugar was solubilized during the contacting step respectively. The % glucose of the hydrolyzate at 24 hours was 65.22% for whole ground corn, 49.64% for endosperm and only 5.79% for refined starch.

TABLE 1

| Grain | Time | BRIX | % Starch Solubilized | Glucose | % DP2 | % DP3 | % DP > 3 |
|---|---|---|---|---|---|---|---|
| Whole corn | 2 | 11.5 | | 31.60 | 21.36 | 13.48 | 33.56 |
| | 4 | 14.0 | | 37.56 | 24.31 | 13.65 | 24.48 |
| | 6 | 16.3 | | 41.33 | 25.42 | 13.36 | 19.88 |
| | 12 | 18.2 | | 46.23 | 26.18 | 12.63 | 14.96 |
| | 24 | 20.0 | 79.1 | 65.22 | 22.50 | 7.36 | 4.92 |
| Endosperm | 2 | 13.4 | | 27.12 | 13.85 | 8.88 | 50.15 |
| | 4 | 16.1 | | 33.01 | 16.45 | 9.39 | 41.15 |
| | 6 | 17.5 | | 36.56 | 18.18 | 9.59 | 35.67 |
| | 12 | 21.7 | | 47.43 | 20.98 | 9.65 | 21.94 |
| | 24 | 22.9 | 71.1 | 49.64 | 21.33 | 9.52 | 19.51 |

TABLE 1-continued

| Grain | Time | BRIX | % Starch Solubilized | Glucose | % DP2 | % DP3 | % DP > 3 |
|---|---|---|---|---|---|---|---|
| Refined Cornstarch | 2 | 14.4 | | 1.40 | 10.37 | 15.27 | 72.96 |
| | 4 | 16.8 | | 2.34 | 11.60 | 15.22 | 70.84 |
| | 6 | 17.8 | | 5.14 | 12.27 | 15.13 | 67.45 |
| | 12 | 19.1 | | 4.94 | 13.21 | 15.62 | 66.22 |
| | 24 | 20.9 | 60.0 | 5.79 | 14.40 | 17.42 | 62.39 |

After 24 hours, using the samples from whole ground corn (32% DS), yeast fermentations were conducted at pH 4.2, 32° C. in the presence of 400 ppm urea; Red Star Red yeast (Fermentus); STARGEN 001; and 0.1 SAPU/g DS protease in a 125 ml flask. HPLC data are illustrated in Table 2.

TABLE 2

| STARGEN 001 GAU/g | % V/V ETOH 24 hrs | % V/V ETOH 48 hrs | % V/V ETOH 72 hrs |
|---|---|---|---|
| 0.1 | 10.11 | 11.74 | 13.64 |
| 0.2 | 10.36 | 12.19 | 14.62 |
| 0.4 | 10.83 | 12.73 | 15.35 |

EXAMPLE 2

Solubilization and Ethanol Production From Milo Granular Starch

Two pretreatments were run: (A) 160 g of whole ground milo having a moisture content of 11.6% and a total starch content of 53.3% was weighed and transferred to a stainless steel vessel containing 340 g water. The pH of the slurry was adjusted to pH 5.5 using 6 N sulphuric acid. SPEZYME Ethyl (1.0 AAU/g DS) was added. The temperature was maintained at 62° C. and 32% DS. (B) HGA was included in the pretreatment as described above in (A) at the equivalent of 0.1 GAU HGA/g DS. The % solubilized solids and % glucose are presented in Table 3.

TABLE 3

| Enzyme | Time (hrs) | % DP1 (glucose) | % DP2 | % DP3 | % DP > 3 | % solublized starch |
|---|---|---|---|---|---|---|
| SPEZYME Ethyl | 2 | 57.71 | 24.60 | 10.42 | 7.27 | |
| | 4 | 64.41 | 22.50 | 9.13 | 3.95 | |
| | 6 | 67.16 | 21.83 | 8.16 | 2.85 | |
| | 24 | 86.50 | 9.91 | 2.95 | 0.63 | 54.7 |
| SPEZYME Ethyl + HGA | 2 | 84.34 | 9.48 | 1.47 | 4.72 | |
| | 4 | 87.72 | 8.07 | 1.18 | 3.03 | |
| | 6 | 88.91 | 7.68 | 1.03 | 2.37 | |
| | 24 | 93.10 | 5.26 | 0.59 | 1.05 | 69.3 |

The feedstock (mash) from the HGA pretreatment described above was evaluated under regular yeast fermentation conditions (e.g. Red Star Yeast, pH 4.2, 32° C. in the presence of 400 ppm urea; STARGEN 001 and 0.05 SAPU/g DS) in a 125 ml flask. HPLC results are illustrated in Table 4.

TABLE 4

| Pre-treatment | GAU/g STARGEN 001 | % V/V Ethanol 24 hrs | % V/V Ethanol 48 hrs |
|---|---|---|---|
| SPEZYME Ethyl + HGA | 0.1 | 10.02 | 11.98 |
| | 0.2 | 10.22 | 12.75 |

EXAMPLE 3

Effect of Temperature on Glucose Production From Whole Ground Milo

Incubation of a 30% ds aqueous slurry of whole ground milo at pH 5.5 containing GC100 (4.0 AAU/g DS) was carried out at 60° C., 65° C. and 70° C. After 6 hours of the incubation, the samples were withdrawn and centrifuged to separate the insolubles. The Brix of the clear supernatant was measured. The oligosaccharide composition (DP2, DP3, and DP>3) of the clear supernatant was determined by HPLC. The % solubilized starch and % glucose were determined and the results are illustrated in Table 5.

TABLE 5

| ° C. | % Solubilized Starch | % W/W DP1 (Glucose) | % W/W DP2 | % W/W DP3 | % W/W DP > 3 |
|---|---|---|---|---|---|
| 60 | 69.9 | 52.48 | 27.07 | 12.08 | 8.36 |
| 65 | 68.2 | 52.61 | 23.42 | 10.41 | 13.56 |
| 70 | 61.9 | 36.49 | 18.98 | 10.27 | 34.26 |

As the incubation temperature increased from 60° C. to 70° C. during the contacting step with whole ground milo, the solubilization of starch and the glucose content decreased. This suggests that the alpha-amylase may be inactivated at 70° C. More than 50% of the solubilized starch was hydrolyzed to glucose at 65° C. suggesting the endogenous plant starch hydrolyzing enzymes are capable of hydrolyzing the soluble oligosaccharides into glucose.

The feedstock from the pretreatment described above at 65° C. was evaluated under regular fermentation conditions as essentially described in example 2; except the % DS was 30. The results are illustrated in Table 6.

TABLE 6

| STARGEN 001 (GAU/g DS) | % V/V ETOH 24 hrs | % V/V ETOH 48 hrs | % V/V ETOH 72 hrs |
|---|---|---|---|
| 0.1 | 9.19 | 11.00 | 11.29 |
| 0.2 | 9.32 | 11.07 | 12.80 |
| 0.4 | 9.61 | 11.47 | 13.32 |

EXAMPLE 4

Solubilization and Ethanol Production From Rice Granular Starch

Rice grain (116 g) having a starch content of 81.5%; a moisture content of 14% and a particle size that passes through a 30 mesh screen was mixed with 284 g of water to make a 25% DS slurry. GC100 (4.0 AAU/g DS) was added to the slurry. The temperature was maintained at 65° C. and pH adjusted to pH 5.5. The Brix was measured at 2, 4 6, and 24 hrs. The % soluble starch and % glucose were determined and the results are illustrated in Table 7.

TABLE 7

| Time hrs | Brix | % solubilized starch | % W/V DP1 (glucose) | % W/V DP2 | % W/V DP3 | % W/V .DP3 |
|---|---|---|---|---|---|---|
| 1 | 11 | 39.2 | 27.5 | 19.8 | 12.7 | 39.6 |
| 2 | 12.5 | 44.6 | 31.2 | 22.2 | 13.4 | 32.6 |
| 4 | 14.8 | 52.8 | 33.4 | 24.0 | 13.8 | 28.7 |
| 6 | 16.2 | 57.5 | 33.8 | 24.4 | 13.9 | 27.7 |
| 24 | 16.4 | 58.4 | 36 | 26.2 | 14.6 | 23.2 |

After 24 hours, yeast fermentations were conducted at pH 4.2, 30° C. in the presence of 0.75 GAU/g DS STARGEN 001, 400 ppm urea, and Angel yeast (Jiangxi, China) at 0.4%. HPLC samples were taken at 24, 48 and 67 hrs (Table 8).

TABLE 8

| Time hrs | % W/V glucose | % V/V ETOH |
|---|---|---|
| 24 | 2.15 | 6.62 |
| 48 | 0.32 | 10.4 |
| 67 | 0.35 | 12.0 |

We claim:

1. A method of producing glucose from a granular starch substrate comprising:
    a) contacting a slurry comprising granular starch obtained from a plant material with an α-amylase at a temperature below the starch gelatinization temperature of the granular starch to produce oligosaccharides and allowing endogenous plant starch hydrolyzing enzymes to hydrolyze said oligosaccharides, and
    b) producing a mash comprising at least 10% glucose, wherein the contacting step is conducted for a period of 5 minutes to 48 hours at a pH of 3.5 to 7.0.

2. The method according to claim 1, wherein the α-amylase is derived from a *Bacillus stearothermophilus*, a *Bacillus licheniformis* or a *Bacillus amyloliquefaciens*.

3. The method according to claim 1, wherein the amount of α-amylase supplied in the contacting step is between 0.01 to 10.0 α-amylase units per gram dry solids content (AAU/g DS).

4. The method according to claim 1, wherein the temperature is between 50° C. and 70° C.

5. The method according to claim 1, wherein the mash comprises at least 30% glucose.

6. The method according to claim 1, wherein the plant material is corn, milo, barley, wheat, rice or combinations thereof.

7. The method according to claim 6, wherein the plant material is fractionated corn.

8. A process for producing ethanol comprising:
    a) contacting a slurry comprising granular starch obtained from plant material with an α-amylase capable of solubilizing granular starch to produce oligosaccharides and allowing endogenous plant starch hydrolyzing enzymes to hydrolyze said oligosaccharides, wherein said contacting is at a pH of 3.5 to 7.0; at a temperature below the starch gelatinization temperature of the granular starch; and for a period of 5 minutes to 24 hours,
    b) obtaining a mash comprising greater than 20% glucose, and c) fermenting said mash in the presence of a fermenting microorganism and starch hydrolyzing enzymes at a temperature of between 10° C. and 40° C. for a period of 10 hours to 250 hours to produce ethanol.

9. The process according to claim 8 further comprising recovering the ethanol.

10. The process according to claim 8, wherein the α-amylase is a bacterial α-amylase.

11. The process according to claim 10, wherein the α-amylase is derived from a *Bacillus stearothermophilus*, a *Bacillus licheniformis* or a *Bacillus amyloliquefaciens*.

12. The process according to claim 8, wherein the contacting step is conducted at a temperature of between 50° C. and 70° C.

13. The process according to claim 8, wherein the contacting step is conducted at a pH of between 5.0 and 6.0.

14. The process according to claim 8, wherein the contacting is for a period of 15 minutes to 12 hours.

15. The process according to claim 8, wherein said mash comprises greater than 30% glucose after contacting between 15 minutes and 6 hours.

16. The process according to claim 8, further comprising clarifying said mash by centrifugation before the fermenting step.

17. The process according to claim 8, further comprising adding additional enzymes to the contacting step.

18. The process according to claim 8, wherein the slurry has between 5-60% DS granular starch.

19. The process of claim 8 further comprising contacting the mash with an aqueous solution comprising backset to dilute the % DS prior to the fermentation step.

20. The process according to claim 8, wherein the granular starch is obtained from corn, milo, barley, wheat, rice or combinations thereof.

21. The process according to claim 12, wherein the temperature is between 60° C. and 70° C.

22. The process according to claim 15, wherein said mash comprises greater than 40% glucose after contacting between 15 minutes and 6 hours.

23. The process according to claim 17, wherein the additional enzymes are selected from the group of glucoamylases, phytases and proteases.

24. The process according to claim 18, wherein the % DS granular starch is between 20-40% DS.

25. The process according to claim 20, wherein the % glucose after 6 hours is 30%.

26. The process according to claim 20, wherein the % glucose after 6 hours is 40%.

27. The process according to claim 23, wherein the additional enzyme is a phytase.

28. The process according to claim 23, wherein the additional enzyme is a protease.

* * * * *